United States Patent [19]
Reeve et al.

[11] Patent Number: 5,849,542
[45] Date of Patent: Dec. 15, 1998

[54] PRIMER EXTENSION MASS SPECTROSCOPY NUCLEIC ACID SEQUENCING METHOD

[75] Inventors: Michael Alan Reeve, Henley-on-Thames; Roland Paul Howe, Great Missenden; Terek Schwarz, Amersham, all of United Kingdom

[73] Assignee: Amersham Pharmacia Biotech UK Limited, Buckinghamshire, United Kingdom

[21] Appl. No.: 640,920

[22] PCT Filed: Nov. 17, 1994

[86] PCT No.: PCT/GB94/02527

§ 371 Date: May 10, 1996

§ 102(e) Date: May 10, 1996

[87] PCT Pub. No.: WO95/14108

PCT Pub. Date: May 26, 1995

[30] Foreign Application Priority Data

| Nov. 17, 1993 | [EP] | European Pat. Off. | 93309176 |
| Jun. 9, 1994 | [GB] | United Kingdom | 9411575 |
| Jul. 28, 1994 | [GB] | United Kingdom | 9415265 |

[51] Int. Cl.⁶ .......................... C12P 19/34; C07H 21/04; G06G 7/58; B01D 59/44
[52] U.S. Cl. .................. 435/91.1; 435/91.2; 536/23.1; 536/24.3; 364/498; 422/82.01; 250/281; 250/287
[58] Field of Search ................................ 435/91.2, 91.1; 536/24.3, 23.1; 364/498; 422/82.01; 250/281, 287

[56] References Cited

U.S. PATENT DOCUMENTS

| 5,108,892 | 4/1992 | Burke et al. ................................. 435/6 |
| 5,221,518 | 6/1993 | Mills ........................................ 422/62 |
| 5,228,644 | 7/1993 | Beavis et al. .............................. 436/94 |

FOREIGN PATENT DOCUMENTS

| 0 360 676 | 3/1990 | European Pat. Off. . |
| WO 94/21822 | 9/1984 | WIPO . |
| WO 89/12694 | 12/1989 | WIPO . |
| WO 92/13629 | 8/1992 | WIPO . |
| WO 94/16101 | 7/1994 | WIPO . |
| WO 95/14108 | 5/1995 | WIPO . |

OTHER PUBLICATIONS

Huth–Fehre, T., et al., "Matrix–Assisted Laser Desorption Mass Spectrometry of Oligodeoxythymidylic Acids", *Rapid Commun. Mass Spectrom.*, 6:209–213 (1992).

Jacobson, Bruce K., et al., "Applications of Mass Spectrometry to DNA Sequencing", *GATA*, 8(8):223–229 (1991).

Nelson, Randall W., et al., "Time–of–Flight Mass Spectrometry of Nucleic Acids by Laser Ablation and Ionization from a Frozen Aqueous Matrix", *Rapid Commun. Mass Spectrom.*, 4(9):348–351 (1990).

Nordhoff, E., et al., "Ion Stability of Nucleic Acids in Infrared Matrix–Assisted Laser Desorption/Ionization Mass Spectrometry", *Nucl. Acids Res.*, 21(15):3347–3357 (1993).

*Primary Examiner*—W. Gary Jones
*Assistant Examiner*—Joyce Tung
*Attorney, Agent, or Firm*—Marshall, O'Toole, Gerstein, Murray & Borun

[57] ABSTRACT

A method of sequencing a target nucleic acid using primer extension mass spectroscopy to generate an observed mass spectrum, on which base calling cycles are carried out using calibrated inter-peak mass difference values such that: each called base allows mass calculation for the base-called peak in the observed mass spectrum; this calculated mass is then used as a further calibration point for subsequent rounds of base calling. A reaction mixture of all four base-specific chain extension nucleotides and four chain termination nucleotide analogues. A method of performing mass spectroscopy, which method comprises subjecting molecular ions which have been chemically charged in a predetermined manner to time-of-flight or Fourier transform mass spectroscopy.

17 Claims, 3 Drawing Sheets

PRIMER EXTENSION MASS SPECTROSCOPY NUCLEIC ACID SEQUENCING METHOD

This application is a 371 of PCT/B94/02527 filed Nov. 17,1994.

INTRODUCTION

Sanger Sequencing:

Conventional (Sanger) nucleic acid sequencing [1] relies upon the hybridisation of an oligonucleotide primer to target nucleic acid. A polymerase is then used to extend this complex into four separate nested sets of extension products terminating in dideoxy base analogues. These nested sets are resolved by size using gel electrophoresis. Various labelling and detection strategies can be employed to read the sequence from the base-specific nested sets. Conventional nucleic acid sequencing is highly skilled, very laborious and the rate of data acquisition is limited by the time consuming gel electrophoresis step.

Sequencing by Hybridisation:

Schemes for nucleic acid sequencing by hybridisation (SBH) [2] rely upon the stringent hybridisation of many oligonucleotide probes (such as all the possible 8 mers) to target nucleic acid. Although elegant, such schemes are critically dependent on the ability to discriminate perfect matches from mismatches. Such discrimination is currently far from a reality. SBH is a compromise between the size of the experiment (65,536 8 mers need to be synthesised to make the complete set) and the quality of the data used to reconstruct the target sequence. The longer the sequence data obtained from each hybridisation, the easier the target sequence is to reconstruct but the larger the number of hybridisations that need to be carried out.

This invention directly addresses a great many of the abovementioned problems.

The Invention

In one aspect the invention provides a method of sequencing a target nucleic acid by using primer extension mass spectroscopy to generate an observed mass spectrum wherein the observed mass spectrum is generated by the steps of:

a) Hybridising at least one oligonucleotide primer to the target nucleic acid so as to form at least one primer-target hybrid, b) Subjecting each primer-target hybrid to polymerase catalysed chain extension conditions in the presence of four chain-extending nucleotides and of four chain-terminating nucleotide analogues, so as to generate a nested set of primer extension products, c) Subjecting each nested set of primer extension products to minimal fragmentation mass spectroscopy so as to generate the observed mass spectrum, wherein the following values are known with certainty: $CM^{-dA-}$, $CM^{-dC-}$, $CM^{-dG-}$, $CM^{-dT-}$, $CM^{-ddA-}$, $CM^{-ddC-}$, $CM^{-ddG-}$, $CM^{-ddT-}$, and CM0 (the mass of the primer used), the calculated value CM0 is used in order to calibrate inter-peak mass difference values (OIPMD) of the observed mass spectrum, base calling cycles are carried out using the calibrated OIPMD values such that:

each called base allows mass calculation for the base-called peak in the observed mass spectrum, this calculated mass is then used as a further calibration point for subsequent rounds of base calling.

In another aspect the invention provides, as a reagent suitable for use in this method though also having other uses, a reaction mixture containing all four base specific chain extension nucleotides which are not labelled so as to be distinguishable from one another, and four chain termination nucleotide analogues which are not labelled so as to be distinguishable from one another.

In another aspect the invention provides, as a technique suitable for use in this method though also having other uses, a method of performing mass spectroscopy, which method comprises subjecting molecular ions which have been chemically charged in a predetermined manner to time-of-flight or Fourier transform mass spectroscopy. This aspect is described below under the heading "Chemically-created Molecular Ions".

BRIEF DESCRIPTION OF DRAWINGS

Reference is directed to the accompanying drawings in which.

PRIMER EXTENSION MASS SPECTROSCOPIC (PEMS) SEQUENCING

Figure 1:
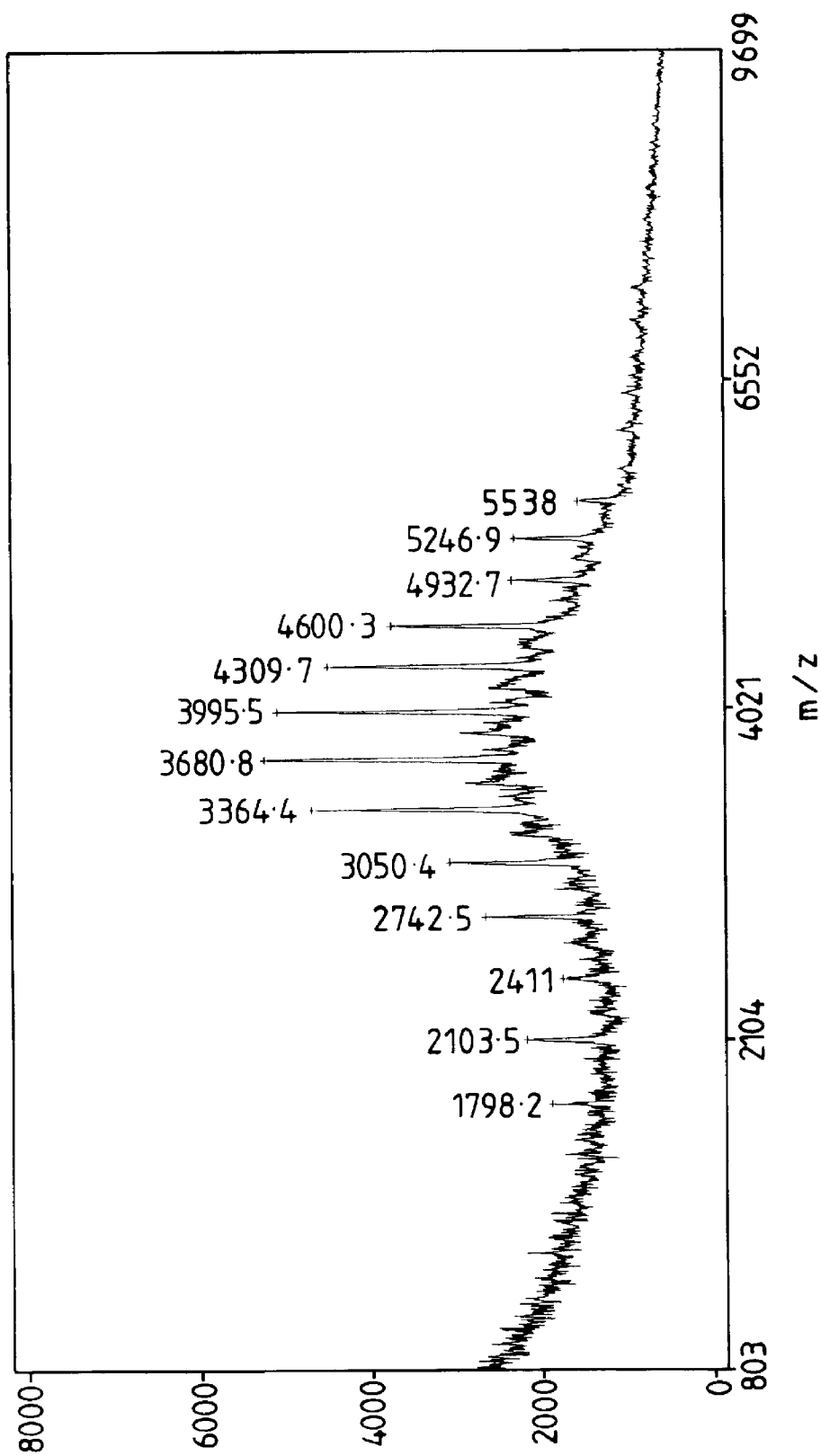
FIG. 1 is a Mass Spectrograph.

PEMS sequencing according to this invention differs from Sanger sequencing and sequencing by hybridisation in that it generates extension products from primers (with all four dNTPs and all four ddNTPs together in one reaction) and thence allows the sequence to be directly read by the observed mass difference between sequential peaks in a mass spectrum. Many hybridisation events may be spatially arrayed, extended in parallel and then sequentially analysed by sequential desorption/ionisation followed by mass spectroscopy.

With the PEMS method, the amount of sequence data obtained from each initial hybridisation is greater than that of just the oligonucleotide used for hybridisation. The amount of sequence data obtained from each initial hybridisation is potentially of the order of 100 or more bases (dependent upon the resolution of the mass spectrometer used for sequence determination). Furthermore, the rate of sequence acquisition with mass spectroscopy is potentially vastly greater than that possible using gel electrophoresis.

The PEMS method gives rise to an observed mass spectrum for the extension fragments. The present invention also relates to a method for determining the order of the bases from a PEMS sequencing observed mass spectrum.

Sequence Reconstruction from Multiple Arrayed Hybridizations:

A number of oligonucleotide primers could be synthesized, hybridized to the target and extended into nested sets in separate reactions. The oligonucleotides could be arranged in a spatial array and simultaneously hybridized to the target. Similarly, the primer extension to generate nested sets from each oligonucleotide primer hybridized to the target could be simultaneously carried out for the whole array. Mass spectroscopic detection would then be sequential for each nested set generated in the array.

Because the amount of sequence generated from each oligonucleotide to target hybridization event in the PEMS method is greater than that of just the oligonucleotide used for hybridization, fewer oligonucleotide to target hybridization events are required in order to reconstruct the target sequence than are required in SBH schemes. In addition, the number of gaps in the sequence (due to branch points) will be considerably less with PEMS sequencing than with SBH schemes.

One further advantage of the PEMS method is the ability to walk along the target for gap filling in the sequence. Oligonucleotide primers corresponding to the end of the readable part of one round of PEMS sequencing can be synthesized (or formed by stacking two or more smaller oligonucleotides) and used for a subsequent round of PEMS sequencing.

TERMINOLOGY

Oligonucleotides:

Oligonucleotides may be DNA or RNA based. They may contain one or more modified residue (modification may be in the base, sugar or backbone moiety or combinations of the above). They may also contain a non-phosphodiester backbone (phoshorothioate, methylphosphonate and nylon backbones are just some examples of non-phosphodiester backbones). Oligonucleotides may also have attached intercalating groups (such as acridine derivatives) in order to stabilize their binding to target molecules.

Target Molecules:

Target molecules may be DNA or RNA based, rendered temporarily, partially or wholly single stranded for the purposes of hybridization. They may be genomic DNA, YACS, P1 clones, cosmids, lambda, plasmids, M13 clones, phagemids, PCR products or chemically synthesized oligonucleotides.

Hybridization:

Oligonucleotides are hybridized to target nucleic acid molecules. Hybridization may be in free solution, with oligonucleotide bound to a solid support or with target bound to a solid support.

Hybridization and/or extension may be carried out within the matrix used for MALDI. Alternatively, Hybridization and/or extension may be carried out elsewhere followed by transfer to the matrix used for MALDI.

Hybridization can be to single oligonucleotides or to multiples of stacked oligonucleotides [3] (these stacks may or may not be stabilized by DNA binding proteins, for example single strand binding proteins).

Primer Extension:

The polymerase for primer extension may be either an RNA- or a DNA- dependent RNA or DNA polymerase. It may be either thermophilic or mesophilic and may be used with Mg, Mn or Mg+Mn based buffer systems.

Generation of a nested set of termination products at all four bases can be achieved by three possible methods:

1. Extension of the primer followed by controlled exonuclease digestion from either the 5' or the 3' end only.
2. Extension of the primer under conditions where the concentration of one or more of the four dNTPs (or, more generally, chain extending analogues) are limiting.
3. Extension of the primer in the presence of all four dNTPs (or, more generally, chain extending analogues) and all four ddNTPs (or, more generally, chain terminating analogues). In this way a nested set of all extension fragments over about 100–200 bases can be obtained from the primer.

dNTPs and/or ddNTPs used for primer extension may be unmodified or they may be modified (either chemically or by isotopic composition) in order to improve the IPMDs (see below) and/or the generation of the nested set from the primer.

The Method:

For each combination of oligonucleotide primer and target, a hybridization reaction is carried out. Primer extension is then carried out using a polymerase. The nested set of extension products generated by this process is then analyzed by mass spectroscopy, as described below, to give the sequence of bases extending from the oligonucleotide primer.

Spatial isolation between each oligonucleotide primer and target hybridization event allows sequential analyses by mass spectroscopy and thus sequential sequence determination to be facilitated.

Matrix Assisted Laser Desorption Ionization (MALDI) [41], Matrix Assisted Laser Desorption Ionization Time-of-Flight Mass SpectroscoTY (MALDI-TOF MS) and Matrix Assisted Laser Desorption Ionization Fourier Transform Mass Spectroscopy (MALDI-FT MS) [5]:

MALDI-TOF MS and MALDI-FT MS are tools for the mass determination of high molecular weight species.

With MALDI, a laser pulse is used to desorb and ionize the species of interest from a matrix in which it is embedded. The desorption and ionization are very mild and produce molecular ions with very few fragmentation products. The very low level of molecular ion fragmentation allows the direct readout of the sequence or residues in the mass spectrum of a nested set originating from the hybridization primer. Any other desorption and ionization method could potentially be used provided that similarly low levels of molecular ion fragmentation could be achieved. Thus, desorption and ionization need not necessarily be limited to matrix assisted laser pulsing.

In TOF MS, the desorbed molecular ions are accelerated in a constant electric field and are detected at the end of a linear tube. The time difference between laser pulse desorption and detection is proportional to the square root of the mass/charge for each molecular ion.

In FT MS, ions are trapped by a combination of magnetic and electostatic fields. The trapped ions are induced into coherent cyclotron motion by a variety of pulsed excitation techniques. The time domain signal produced after this excitation is then Fourier Transformed to give a spectrum of abundance against mass/charge for each molecular ion.

Desorption, ionisation and molecular ion fragmentation are very much dependent upon: the nature of the matrix, the concentration of the matrix, the nature of the species of interest, the concentration of the species of interest, the nature of the buffer, the concentration of various buffer components, the co-crystallisation of the matrix and species of interest and the laser power used for the pulse. The MALDI technique also generally requires a high ratio of matrix to species of interest thus compromising sensitivity. Much work is generally required in order to optimise all of the above factors.

In addition to the above, the laser pulse gives rise to a cloud of molecular ions that do not all have exactly the same initial spatial locations or initial kinetic energies. The non-identical initial spatial locations and nonidentical initial kinetic energies of the molecular ions combine to limit the available resolution of the subsequent mass spectroscopy.

The Inter Peak Mass Difference (IPMD):

Let the mass of a given extension product r residues long be $M_r$.

Let the mass of the extension product r-1 residues long be $M_r-1$

The Inter Peak Mass Difference ($IPMD_r$) for residue r is defined as:

$$(IPMD_r)=(M_r)-(M_r-1)$$

Let the mass increase to the extension product by adding an A-specific chain terminating residue at the 3' end of the extension product be $M^{-ddA}$.

Let the mass increase to the extension product by adding an C-specific chain terminating residue at the 3' end of the extension product be $M^{-ddC}$.

Let the mass increase to the extension product by adding an G-specific chain terminating residue at the 3' end of the extension product be $M^{-ddG}$.

Let the mass increase to the extension product by adding an T-specific chain terminating residue at the 3' end of the extension product be $M^{-ddT}$.

Let the mass added to the extension product by adding a A-specific chain extending residue between the primer and the 3' end of a chain terminated extension product be $M^{-dA-}$.

Let the mass added to the extension product by adding a C-specific chain extending residue between the primer and the 3' end of a chain terminated extension product be $M^{-dC-}$.

Let the mass added to the extension product by adding a G-specific chain extending residue between the primer and the 3' end of a chain terminated extension product be $M^{-dG-}$.

Let the mass added to the extension product by adding a T-specific chain extending residue between the primer and the 3' end of a chain terminated extension product be $M^{-dT-}$.

EXAMPLE

| | |
|---|---|
| primer-dA-dC-dG-dT-dA-dT-dG----- | primer (synthesized strand) |
| -------dT-dG-dC-dA-dT-dA-dC------ | target nucleic acid (template strand) |
| Extension Product: | $(IPMD_r) = (M_r) - (M_{r-1})$ |
| primer-dA-dC-dG-dT-dA-dT-ddG | $IPMD_{r=7} = (M^{-ddG}) + (M^{-dT-}) - (M^{-ddT})$ |
| primer-dA-dC-dG-dT-dA-ddT | $IPMD_{r=6} = (M^{-ddT}) + (M^{-dA-}) - (M^{-ddA})$ |
| primer-dA-dC-dG-dT-ddA | $IPMD_{r=5} = (M^{-ddA}) + (M^{-dT-}) - (M^{-ddT})$ |
| primer-dA-dC-dG-ddT | $IPMD_{r=4} = (M^{-ddT}) + (M^{-dG-}) - (M^{-ddG})$ |
| primer-dA-dC-ddG | $IPMD_{r=3} = (M^{-ddG}) + (M^{-dC-}) - (M^{-ddC})$ |
| primer-dA-ddC | $IPMD_{r=2} = (M^{-ddC}) + (M^{-dA-}) - (M^{-ddA})$ |
| primer-ddA | $IPMD_{r=1} = (M^{-ddA})$ |
| primer | |

For the simplest case, where dNTP and ddNTPs residues made up from 12C, 14N, 16O, 31P, 1H, which have not been modified in any way are used, we have:

M-ddA=297.0627
M-ddC=273.0515
M-ddG=313.0576
M-ddT=288.0511
M-dA-=313.0576
M-dC-=289.0464
M-dG-=329.0525
M-dT-=304.0460 (the backbone phosphate is considered to be un-ionised for the purposes of this example).
and the above values for IPMDs simplify to:

| | |
|---|---|
| primer-dA-dC-dG-dT-dA-dT-dG----- | primer (synthesized strand) |
| -------dT-dG-dC-dA-dT-dA-dC------ | target nucleic acid (template strand) |
| Extension Product: | $(IPMD_r) = (M_r) - (M_{r-1})$ |
| primer-dA-dC-dG-dT-dA-dT-ddG | $IPMD_{r=7} = (M^{-dG-})$ |
| primer-dA-dC-dG-dT-dA-ddT | $IPMD_{r=6} = (M^{-dT-})$ |
| primer-dA-dC-dG-dT-ddA | $IPMD_{r=5} = (M^{-dA-})$ |
| primer-dA-dC-dG-ddT | $IPMD_{r=4} = (M^{-dT-})$ |
| primer-dA-dC-ddG | $IPMD_{r=3} = (M^{-dG-})$ |
| primer-dA-ddC | $IPMD_{r=2} = (M^{-dC-})$ |
| primer-ddA | $IPMD_{r=1} = (M^{-ddA})$ |
| primer | |

The sequence of the extension product can thus be read directly from the values of $IPMD_r$ for the mass spectroscopic peaks in the order of increasing mass from the primer.

Several techniques can be used in order to improve the process of sequence reading from the observed mass spectrum.

Firstly, the ratio of signal to noise from the observed mass spectrum can be greatly improved by the summation of several spectra from the original sample. This is possible with MALDI if the sample surface area is larger than the area over which the laser pulse can be focussed.

Secondly, statistical techniques can be used to calibrate the observed mass spectrum using known molecular masses. These techniques will now be described.

The Calculated and Observed Inter Peak Mass Differences (CIPMD and OIPMD):

Let the calculated mass of a given extension product r residues long be CMr.

Let the observed mass of a given extension product r residues long be OMr

Let the calculated mass of the extension product r−1 residues long be CMr−1

Let the observed mass of the extension product r−1 residues long be OMr−1

Let the calculated mass of the primer (extension product r=0 residues long) be CM0.

Let the observed mass of the primer (extension product r=0 residues long) be OM0

The Calculated Inter Peak Mass Difference (CIPMDr) for residue r is defined as: ( CIPMDr)=(CMr)−(CMr−1)

The Observed Inter Peak Mass Difference (OIPMDr) for residue r is defined as:

(OIPMDr)=(OMr)−(OMr−1)

Let the calculated mass increase to the extension product by adding an A-specific chain terminating residue at the 3' end of the extension product be CM-ddA Let the calculated mass increase to the extension product by adding an C-specific chain terminating residue at the 3' end of the extension product be CM-ddC Let the calculated mass increase to the extension product by adding an G-specific chain terminating residue at the 3' end of the extension product be CM-ddG Let the calculated mass increase to the extension product by adding an T-specific chain terminating residue at the 3' end of the extension product be CM-ddT Let the calculated mass added to the extension product by adding a A-specific chain extending residue between the primer and the 3' end of a chain terminated extension product be CM-dA- Let the calculated mass added to the extension product by adding a C-specific chain extending residue between the primer and the 3' end of a chain terminated extension product be CM-dC- Let the calculated mass added to the extension product by adding a G-specific chain extending residue between the primer and the 3' end of a chain terminated extension product be CM-dG- Let the calculated mass added to the extension product by adding a T-specific chain extending residue between the primer and the 3' end of a chain terminated extension product be CM-dT- In the above example, where dNTP and ddNTPs residues made up from 12C, 14N, 16O, 31P, 1H, which have not been modified in any way are used, the observed mass spectrum will consist of the following fragments:

| | |
|---|---|
| primer-dA-dC-dG-dT-dA-dT-dG----- | primer (synthesized strand) |
| -------dT-dG-dC-dA-dT-dA-dC------ | target nucleic acid (template strand) |

| Extension Product: | OMr | (OIPMDr) = (OMr) − (OMr − 1) |
|---|---|---|
| primer-dA-dC-dG-dT-dA-dT-ddG | OM7 | OIPMD7 |
| primer-dA-dC-dG-dT-dA-ddT | OM6 | OIPMD6 |
| primer-dA-dC-dG-dT-ddA | OM5 | OIPMD5 |
| primer-dA-dC-dG-ddT | OM4 | OIPMD4 |
| primer-dA-dC-ddG | OM3 | OIPMD3 |
| primer-dA-ddC | OM2 | OIPMD2 |
| primer-ddA | OM1 | OIPMD1 |
| primer | OM0 | |

For the following example, the following values are known with certainty:

CM-dA-, CM-dC-, CM-dG-, CM-dT-, CM-ddA-, CM-ddC-, CM-ddG-, CM-ddT- and CM0 (the mass of the primer used).

Let us also assume that the first residue to be incorporated is also known from the sequence of the primer binding site. CM1 is therefore also known with certainty.

The calculated values CM0 and CM1 can be used in order to calibrate the observed mass spectrum. As bases are called from the calibrated OIPMD values, more masses can be calculated from the called sequence. More calibration points thus become available for the base calling algorithm.

Working through the above example, we have:

Step 1:

| Extension Product: | OMr |
|---|---|
| primer | OM0 |

OM0 appears at a given point in the mass spectrum.

CM0 is known with certainty and allows the observed mass spectrum to be calibrated.

Step 2:

| Extension Product: | OMr | (OIPMDr) = (OMr) − (OMr − 1) |
|---|---|---|
| primer-ddA | OM1 | OIPMD1 |

OM1 appears at a given point in the mass spectrum.

CM1 is known with certainty and allows the observed mass spectrum to be calibrated.

Two observed masses (OM0 and OM1) and two calculated masses (CM0 and CM1) are thus known.

Step 3:

| Extension Product: | OMr | (OIPMDr) = (OMr) − (OMr − 1) |
|---|---|---|
| primer-dA-ddC | OM2 | OIPMD2 |

OM2 appears at a given point in the mass spectrum (now calibrated using CM0 and CM1 as reference points)

There are four possible values for IMPD2. These are CM-dA-, CM-dC-, CM-dG- and CM-dT- Comparison between the OIPMD2 (in the calibrated mass spectrum) and the calculated values CM-dA-, CM-dC-, CM-dG- and CM-dT- is used to assign the second base in the extension CM2 is now known with certainty. CM0 and CM1 are also known with certainty. These three values therefore allow the observed mass spectrum to be more extensively calibrated in order to further increase its accuracy Step 4:

| Extension Product: | OMr | (OIPMDr) = (OMr) − (OMr − 1) |
|---|---|---|
| primer-dA-dC-ddG | OM3 | OIPMD3 |

OM3 appears at a given point in the mass spectrum (now calibrated using CM0, CM1 and CM2 as reference points)

There are four possible values for IMPD3. These are CM-dA-, CM-dC-, CM-dG- and CM-dT- Comparison between the OIPMD3 (in the calibrated mass spectrum) and the calculated values CM-dA-, CM-dC-, CM-dG- and CM-dT- is used to assign the third base in the extension CM3 is now known with certainty. CM0, CM1 and CM2 are also known with certainty. These four values therefore allow the observed mass spectrum to be more extensively calibrated in order to further increase its accuracy Step 5:

| Extension Product: | OMr | (OIPMDr) = (OMr) − (OMr − 1) |
|---|---|---|
| Primer-dA-dC-dG-ddT | OM4 | OIPMD4 |

OM4 appears at a given point in the mass spectrum (now calibrated using CM0, CM1, CM2 and CM3 as reference points)

There are four possible values for IMPD4. These are CM-dA-, CM-dC-, CM-dG- and CM-dT- Comparison between the OIPMD4 (in the calibrated mass spectrum) and the calculated values CM-dA-, CM-dC-, CM-dG- and CM-dT- is used to assign the fourth base in the extension CM4 is now known with certainty. CM0, CM1, CM2 and CM3 are also known with certainty. These five values therefore allow the observed mass spectrum to be more extensively calibrated in order to further increase its accuracy Step 6:

| Extension Product: | OMr | (OIPMDr) = (OMr) − (OMr − 1) |
|---|---|---|
| primer-dA-dC-dG-dT-ddA | OM5 | OIPMD5 |

OM5 appears at a given point in the mass spectrum (now calibrated using CM0, CM1, CM2, CM3 and CM4 as reference points)

There are four possible values for IMPD5. These are CM-dA-, CM-dC-, CM-dG- and CM-dT- Comparison between the OIPMD5 (in the calibrated mass spectrum) and the calculated values CM-dA-, CM-dC-, CM-dG- and CM-dT- is used to assign the fifth base in the extension CM5 is now known with certainty. CM0, CM1, CM2, CM3 and CM4 are also known with certainty. These six values therefore allow the observed mass spectrum to be more extensively calibrated in order to further increase its accuracy Step 7:

| Extension Product: | OMr | (OIPMDr) = (OMr) − (OMr − 1) |
|---|---|---|
| primer-dA-dC-dG-dT-dA-ddT | OM6 | OIPMD6 |

OM6 appears at a given point in the mass spectrum (now calibrated using CM0, CM1, CM2, CM3, CM4 and CM5 as reference points)

There are four possible values for IMPD6. These are CM-dA-, CM-dC-, CM-dG- and CM-dT- Comparison between the OIPMD6 (in the calibrated mass spectrum) and the calculated values CM-dA-, CM-dC-, CM-dG- and CM-dT- is used to assign the sixth base in the extension CM6 is now known with certainty. CM0, CM1, CM2, CM3, CM4 and CM5 are also known with certainty. These seven values therefore allow the observed mass spectrum to be more extensively calibrated in order to further increase its accuracy Step 8:

| Extension Product: | OMr (OIPMDr) = (OMr) − (OMr − 1) |
|---|---|
| primer-dA-dC-dG-dT-dA-dT-ddG | OM7 OIPMD7 |

OM7 appears at a given point in the mass spectrum (now calibrated using CM0, CM1, CM2, CM3, CM4, CM5 and CM6 as reference points)

There are four possible values for IMPD7.

These are CM-dA-, CM-dC-, CM-dG- and CM-dT-

Comparison between the OIPMD7 (in the calibrated mass spectrum) and the calculated values CM-dA-, CM-dC-, CM-dG- and CM-dT- is used to assign the seventh base in the extension CM7 is now known with certainty. CM0, CM1, CM2, CM3, CM4, CM5 and CM6 are also known with certainty. These eight values therefore allow the observed mass spectrum to be more extensively calibrated in order to further increase its accuracy.

In the above example, all available information has been used in order to calibrate the observed mass spectrum. The amount of data used for base calling thus increases with the length of sequence called. The present invention can in one embodiment use all available data for base calling (whereupon calibration of the observed mass spectrum actually improves for base calling further from the sequencing primer). The present invention can also use only a selected number of bases prior to the base about to be called for calibration and base calling. For this latter process, a rolling local calibration can be carried out for each base called (with a fixed number of bases prior to the base about to be called being used for the calibration used for base calling).

In the above example, CM0 and CM1 were known with certainty and were used in order to initially calibrate the observed mass spectrum. Other peaks of known mass in the mass spectrum obvious to those skilled in the art could be chosen for the calibration (including calibration compounds of known mass not taking part of the PEMS sequencing reaction).

The algorithm for calling the bases from the observed mass spectrum of a PEMS sequencing reaction could be written such that the confidence of base calling is measured by the closeness between the values for CM-dA-, CM-dC-, CM-dG-, CM-dT- and the calibrated OIPMD values.

References

[1] Sanger Sequencing: Molecular Cloning, A Laboratory Manual, 2nd edition, J. Sambrook, E. Fritsch and T. Maniatis, Cold Spring Harbour Laboratory Press, 1989.
[2] Sequencing By Hybridization: Drmanac et al, Science, 260, p1649, (1993)
[3] Stacked Oligos: J. Kieleczawa et al, Science 258, p1787, (1992).
[4] MALDI: F. Hillenkamp et al, Anal. Chem., 63, p1193A, (1991).
[5] Mass Spectrometry: D. Skoog & J. Leary, Principles of Instrumental Analysis, p420, Harcourt Brace Janovich, 4th Edition (1992).

Example

The following oligodeoxyribonucleotides were synthesised:
ACGACG
ACGACGT
ACGACGTG
ACGACGTGT
ACGACGTGTA
ACGACGTGTAA
ACGACGTGTAAA
ACGACGTGTAAAA
ACGACGTGTAAAAC
ACGACGTGTAAAACG
ACGACGTGTAAAACGA
ACGACGTGTAAAACGAC 1 pmol of an equimolar mixture of the above oligos in a volume of 1 µl was mixed with equal volumes of saturated aqueous 2,4,6-trihydroxyacetophenone and saturated aqueous diammonium hydrogen citrate, air dried and laser desorbed/ionised using a Vested 1.2 m Benchtop Time of Flight Mass Spectrometer with 24 kV accelerating voltage and a pressure of $3.34 \times 10^{-7}$ Torr.

79 laser shots were averaged and the observed masses were obtained after rough calibration of the instrument using protein calibration standards. The observed mass spectrum is shown in FIG. 1.

Figure 2:
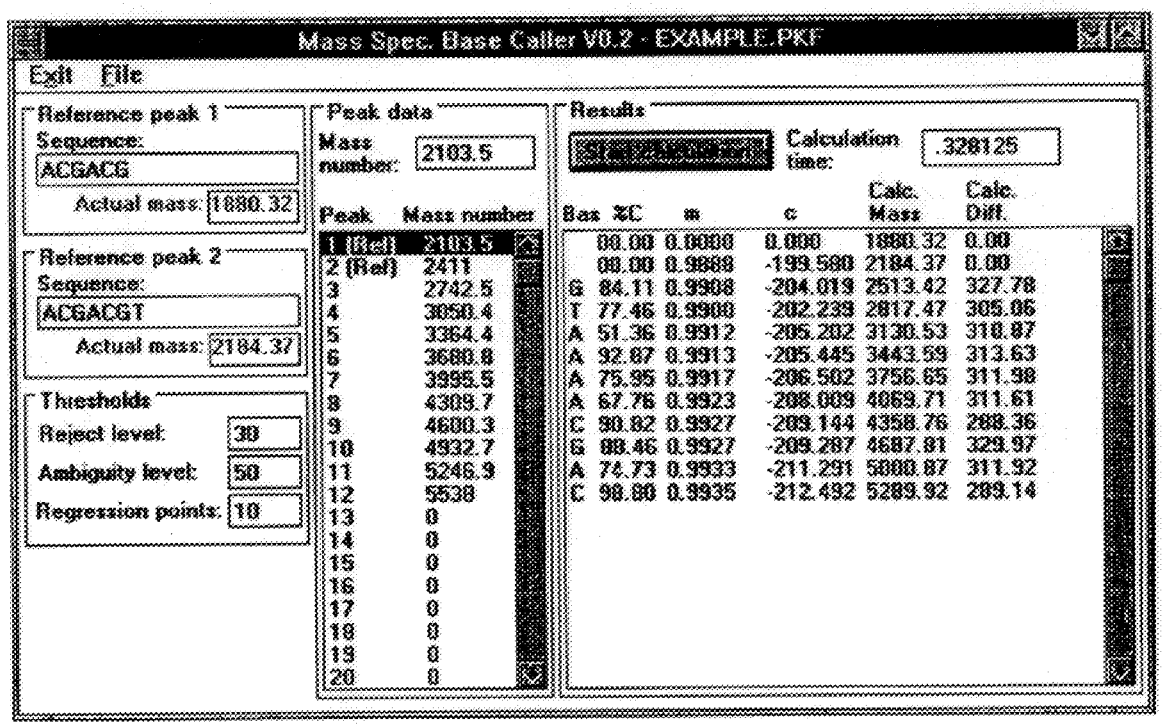
FIG. 2 is a Base Calling Program.

The mass values for peaks in the observed mass spectrum were used as the inputs for the base calling program the results of which are shown in FIG. 2. As can be seen from the figure, the base calling program both calls the correct sequence of bases and gives a confidence value for the calling of each base.

Figure 3:
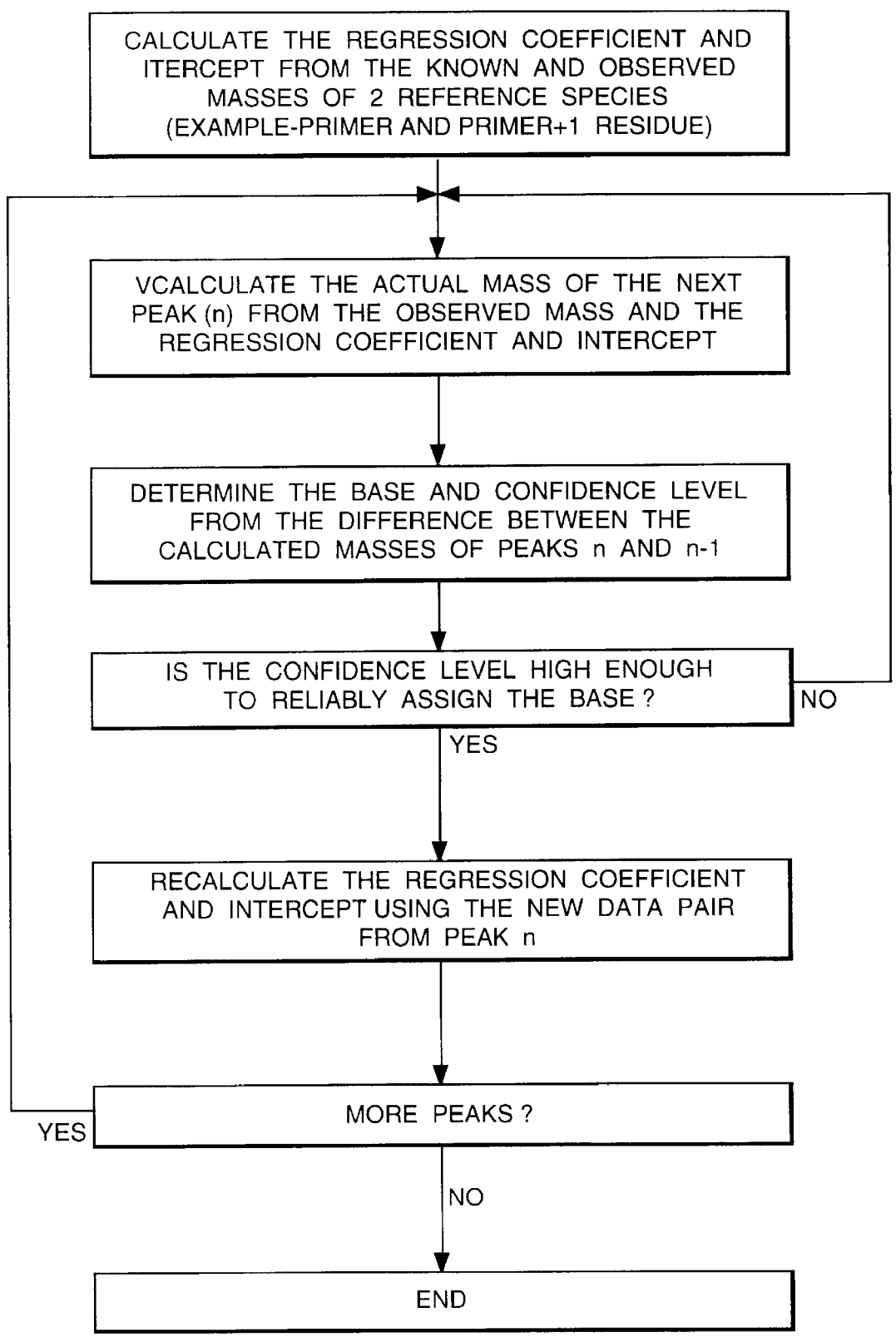
FIG. 3 is a Flow Diagram for the Program of FIG. 2.

FIG. 3 gives a flow diagram for the base calling program the results of which are reported in FIG. 2.

Base calling algorithm computer program.

The steps below describe the algorithm functions used. The actual Microsoft Windows program output is shown in FIG. 2 and the function is shown in flow diagram form in FIG. 3. This program is an example only, and other ways of performing the functions such as calibration or confidence level calculation could easily be devised.

Step 1

Assume that the first two peaks in the mass spectrum have known base sequences and thus known masses. Using normal linear regression, calculate the regression coefficient and intercept of the regression line from the observed and calculated masses of the first two peaks. This calibrates the first part of the observed mass spectrum.

Step 2

Designate the next peak as peak n. Take the observed mass of peak n and use the regression coefficient and intercept (calibration) to calculate the mass.

Step 3

Determine the difference in calculated mass between peaks n and n−1.

Step 4

Compare the mass difference calculated in step 3 to the expected mass differences for the addition of an A, C, G or T residue to the chain. Provisionally assign the relevant base on the basis of whichever is closest.

Step 5

Determine a confidence level for the assignation of the base to the mass difference using the following procedure:

The diagram below shows the expected mass differences for the addition of an A, C, G or T residue. It also shows the mass at the mid point between expected mass and upper and lower points based on the mid point mass differences.

```
------------------------------------------------ 337.04
G ------------------------------------- 329.05
------------------------------------------------ 321.06
A ------------------------------------- 313.06
------------------------------------------------ 308.55
T ------------------------------------- 304.05
------------------------------------------------ 296.55
C ------------------------------------- 289.05
------------------------------------------------ 281.55
```

As described in step 4, the base is provisionally assigned on the basis of whichever is closest. Thus if the mass difference is between 321.06 and 308.55, the base will be assigned as an A.

The confidence level is assigned as the proportion of the difference between the relevant mid, upper or lower point and the A, C, G or T value. Thus a mass difference of 311.98 will be assigned as an A with a confidence of 75.95% because it is 75.95% of the distance between 308.55 and 313.06.

Step 6

Using a threshold value specified by the operator of the software, define whether the confidence level is such that the base is called unambiguously, called ambiguously or rejected.

Step 7

If the base has been accepted, recalculate the calibration using the observed mass and the mass calculated in step 2 as another data pair. If the base is rejected then continue to use the previous calibration.

The number of data pairs used in the regression calculation can be specified by the software operator, this can be designated as r. Thus only the data from peaks n–r to n (or 0 to n) would be used.

Step 8

If there is another peak in the spectrum then return to step 2.

Chemically-created Molecular Ions

In another aspect of this invention, molecular ions are created CHEMICALLY. These chemically-created molecular ions are charged in a predetermined manner. The molecular ions are then desorbed into a vacuum from a solid surface (under conditions that do not cause molecular ion fragmentation) for subsequent mass spectrometry.

In one embodiment, the primer used for extension in a sequencing reaction (either Sanger [1] or PEMS Sequencing) is covalently attached to a stably charged group at the 5' end (or internally, if this does not interfere with hybridisation and/or polymerase extension from the primer/template complex). The stably charged group is 'stable' in that its charge is not dependent upon the local pH conditions. One example of such a stably charged group is a quaternary ammonium group. The charge on the stably charged group may be either positive or negative. The charge may be either z+ or z–, where z is greater than or equal to 1.

There are many ways of attaching a stable charge, such as a quaternary ammonium group, to a primer which will be obvious to those skilled in the art. The following chemical synthetic strategies will serve as just some of many possible examples:

i) Synthesis of an Amino link 2 (Applied Biosystems) terminated primer followed by ammonia deprotection to give a primary amino group at the 5' end of the primer. Coupling of the primary amino group to the quaternary ammonium compound betaine using the carbodiimide coupling reagent EDC (Pierce Chemicals).

ii) Synthesis of an Amino link 2 (Applied Biosystems) terminated primer followed by ammonia deprotection to give a primary amino group at the 5' end of the primer. Coupling of the primary amino group to the quaternary ammonium compound 2-aminoethyl trimethylammonium chloride using the amine-reactive homobifunctional coupling reagent DSS (Pierce Chemicals).

iii) Synthesis of an Amino link 2 (Applied Biosystems) terminated primer followed by ammonia deprotection to give a primary amino group at the 5' end of the primer. Coupling of the primary amino group to the quaternary ammonium compound 2-aminoethyl trimethylammonium chloride using the amine-reactive homobifunctional coupling reagent DMA (Pierce Chemicals).

iv) Synthesis of a C6 thiol linker (Amersham International, RPN2112) terminated primer followed by ammonia deprotection to give a thiol group at the 5' end of the primer. Coupling of the thiol group to the quaternary ammonium compound 2-aminoethyl trimethylammonium chloride using the heterobifunctional coupling reagent Sulfo-LC-SPDP (Pierce Chemicals).

v) Synthesis of a primer followed by ammonia deprotection to give a hydroxyl group at the 5' end of the primer. Phosphorylation of the 5' hydroxyl group using T4 polynucleotide kinase and ATP gamma thiophosphate. Coupling of the thiol moiety of the thiophosphate group to the quaternary ammonium compound 2-aminoethyl trimethylammonium chloride using the heterobifunctional coupling reagent Sulfo-LC-SPDP (Pierce Chemicals).

In a second embodiment, each of the ddNTPs (or, more generally, chain terminating analogues) used for chain termination in a sequencing reaction (either Sanger [1] or PEMS Sequencing) is covalently attached to a stably charged group. The stably charged group is 'stable' in that its charge is not dependent upon the local pH conditions. One example of such a stably charged group is a quaternary ammonium group. The charge on the stably charged group may be either positive or negative. The charge may be either z+ or z–, where z is greater than or equal to 1.

There are many ways of attaching a stable charge, such as a quaternary ammonium group, to a ddNTP which will be obvious to those skilled in the art. The following chemical synthetic strategies will serve as just some of many possible examples:

i) Synthesis of a 3"-amino-1"-propynyl derivative of the ddNTP (e.g. 7-(3"-amino-1"-propynyl)-7-deaza-2',3'-dideoxyadenosine triphosphate, 5-(3"-amino-1"-propynyl)-2',3'-dideoxycytidine triphosphate, 7-(3"-amino-1"-propynyl)-7 deaza-2',3'-dideoxyguanosine triphosphate or 5-(3"-amino-1"-propynyl)-2',3'-dideoxyuridine triphosphate). Coupling of the 3"-amino-1"-propynyl primary amino group to the quaternary ammonium compound betaine using the carbodiimide coupling reagent EDC (Pierce Chemicals).

ii) Synthesis of a 3"-amino-1"-propynyl derivative of the ddNTP (e.g. 7-(3"-amino-1"-propynyl)-7-deaza-2',3'-dideoxyadenosine triphosphate, 5-(3"-amino-1"-propynyl)-2',3'-dideoxycytidine triphosphate, 7-(3"-amino-1"-propynyl)-7 deaza-2',3'-dideoxyguanosine triphosphate or 5-(3"-amino-1"-propynyl)-2',3'-dideoxyuridine triphosphate). Coupling of the 3"-amino-1"-propynyl primary amino group to the quaternary ammonium compound 2-aminoethyl trimethylammonium chloride using the amine-reactive homobifunctional coupling reagent DSS (Pierce Chemicals).

iii) Synthesis of a 3"-amino-1"-propynyl derivative of the ddNTP (e.g. 7-(3"-amino-1"-propynyl)-7-deaza-2',3'-dideoxyadenosine triphosphate, 5-(3"-amino-1"-propynyl)-2',3'-dideoxycytidine triphosphate, 7-(3"-amino-1"-propynyl)-7 deaza-2',3'-dideoxyguanosine triphosphate or 5-(3"-amino-1"-propynyl)-2',3'-dideoxyuridine triphosphate). Coupling of the primary amino group to the quaternary ammonium compound 2-aminoethyl trimethylammonium chloride using the amine-reactive homobifunctional coupling reagent DMA (Pierce Chemicals).

In a third embodiment, one of the dNTPs (or, more generally, chain extending analogues) used for chain extension in a sequencing reaction (either Sanger [1] or PEMS Sequencing) is covalently attached to a stabley charged group. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a dNTP which will be obvious to those skilled in the art. The following chemical synthetic strategies will serve as just some of many possible examples:

i) Synthesis of a 3"-amino-1"-propynyl derivative of the dNTP (e.g. 7-(3"-amino-1"-propynyl)-7-deaza-2'-deoxyadenosine triphosphate, 5-(3"-amino-1"-propynyl)-2'-deoxycytidine triphosphate, 7-(3"-amino-1"-propynyl)-7 deaza-2'-deoxyguanosine triphosphate or 5-(3"-amino-1"-propynyl)-2'-deoxyuridine triphosphate). Coupling of the 3"-amino-1"-propynyl primary amino group to the quaternary ammonium compound betaine using the carbodiimide coupling reagent EDC (Pierce Chemicals).

ii) Synthesis of a 3"-amino-1"-propynyl derivative of the dNTP (e.g. 7-(3"-amino-1"-propynyl)-7-deaza-2'-deoxyadenosine triphosphate, 5-(3"-amino-1"-propynyl)-2'-deoxycytidine triphosphate, 7-(3"-amino-1"-propynyl)-7 deaza-2 -deoxyguanosine triphosphate or 5-(3"-amino-1"-propynyl)-2'-deoxyuridine triphosphate). Coupling of the 3"-amino-1"-propynyl primary amino group to the quaternary ammonium compound 2-aminoethyl trimethylammonium chloride using the amine-reactive homobifunctional coupling reagent DSS (Pierce Chemicals).

iii) Synthesis of a 3"-amino-1"-propynyl derivative of the dNTP (e.g. 7-(3"-amino-1"-propynyl)-7-deaza-2'-deoxyadenosine triphosphate, 5-(3"-amino-1"-propynyl)-2'-deoxycytidine triphosphate, 7-(3"-amino-1"-propynyl)-7 deaza-2'-deoxyguanosine triphosphate or 5-(3"-amino-1"-propynyl)-2'-deoxyuridine triphosphate). Coupling of the primary amino group to the quaternary ammonium compound 2-aminoethyl trimethylammonium chloride using the amine-reactive homobifunctional coupling reagent DMA (Pierce Chemicals).

In a fourth embodiment, The primer used for extension on a template is covalently attached to a stably charged group at the 5' end (or internally, if this does not interfere with hybridisation and/or polymerase extension from the primer/template complex). This extension reaction may be part of a Polymerase Chain Reaction (PCR). The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a primer which will be obvious to those skilled in the art. The chemical synthetic strategies outlined above will serve as just some of many possible examples.

In a fifth embodiment, one of the ddNTPs (or, more generally, chain terminating analogues) used for chain termination is covalently attached to a stably charged group. This chain terminating analogue is then used for 3' end labelling of a nucleic acid molecule with terminal deoxynucleotidyl transferase. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a ddNTP which will be obvious to those skilled in the art. The chemical synthetic strategies outlined above will serve as just some of many possible examples.

In a sixth embodiment, one of the ddNTPs (or, more generally, chain terminating analogues) used for chain termination is covalently attached to a stably charged group. This chain terminating analogue is then used for recessed 3' end labelling ('fill-in' labelling [1]) of a partially double stranded nucleic acid molecule with a polymerase. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a ddNTP which will be obvious to those skilled in the art. The chemical synthetic strategies outlined above will serve as just some of many possible examples.

In a seventh embodiment, one of the dNTPs (or, more generally, chain extending analogues) used for chain extension is covalently attached to a stably charged group. This chain extending analogue is then used for recessed 3' end labelling ('fill-in' labelling [1]) of a partially double stranded nucleic acid molecule with a polymerase and the other three dNTPs not attached to stably charged groups. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a dNTP which will be obvious to those skilled in the art. The chemical synthetic strategies outlined above will serve as just some of many possible examples.

In an eighth embodiment, one of the dNTPs (or, more generally, chain extending analogues) used for chain extension is covalently attached to a stably charged group. This chain extending analogue is then used for incorporation labelling during primer extension with a polymerase. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a dNTP which will be obvious to those skilled in the art. The chemical synthetic strategies outlined above will serve as just some of many possible examples.

In an ninth embodiment, a single stranded nucleic acid fragment (which may be an oligonucleotide primer) is covalently attached to a stably charged group by any of the above methods. The stably charged single stranded nucleic acid fragment is then used in a hybridisation reaction with nucleic acid(s) (some or all of which contain sequence complementary to the single stranded nucleic acid fragment). After the hybridisation reaction, the stably charged single stranded nucleic acid fragment and its hybridised complement are covalently crosslinked (either by an exogeneous crosslinking reagent or by a crosslinking moiety on the stably charged single stranded nucleic acid fragment). The covalently crosslinked complex is then analysed by mass spectroscopy. The stably charged group is 'stable' in that its charge is not dependent upon the local pH conditions. One example of such a stably charged group is a quaternary ammonium group. The charge on the stably charged group may be either positive or negative. The charge may be either z+ or z−, where z is greater than or equal to 1.

There are many ways of attaching a stable charge, such as a quaternary ammonium group, to a nucleic acid fragment which will be obvious to those skilled in the art. The chemical synthetic strategies outlined above will serve as just some of many possible examples.

In each of the above embodiments, the charge on the phosphate backbone of the extension product can be removed by controlled chemical modification (such as alkylation or arylation).

In each of the above embodiments, the charge on the phosphate backbone of the extension product can also be removed by forming the ammonium salt of the phosphate backbone and then subjecting the extension product to a vacuum (wherein the ammonium ions protonate the phosphates, evaporate as ammonia and produce the acid form of the phosphate backbone).

In each of the above embodiments, the extension products thus consist of a stably charged group covalently attached to the molecule of interest (charge may be either z+ or z−) and the chemically modified or acid form of the phosphate backbone (both of which are uncharged). All the extension products are thus molecular ions with the same charge on each molecular ion (either z+ or z−). m/z for each species is thus directly related to mass. For the third and eighth embodiments above, conditions will need to be empirically determined such that the same number of charged dNTPs (preferably one) is incorporated in each extension product.

These molecular ions may be applied to a solid surface, conveniently in solution in a volatile solvent which is afterwards removed by evaporation. They may be applied alone or in admixture with a matrix material.

Desorption of these molecular ions into a vacuum from the solid surface is a prerequisite for mass spectroscopic analysis of the molecular ions.

Two methods are envisaged for the desorption of these molecular ions:

Localised heating brought about by laser, or other, irradiation.

Charge repulsion between the stably charged group and the solid surface to which it is attached.

A combination of these two approaches can also be envisaged.

In the latter method, the solid surface could be one of the electrodes for molecular ion acceleration in a TOF mass spectrometer. This would ensure that all of the molecular ions started out from known positions (i.e. the electrode surface, which could be planar and in the same plane a the TOF detector) and with identical initial kinetic energies. These two factors should combine to greatly improve the resolution of the mass spectrometer.

We claim:

1. A method of sequencing a target nucleic acid by using primer extension mass spectroscopy to generate an observed mass spectrum wherein the observed mass spectrum is generated by the steps of:

a) hybridising at least one oligonucleotide primer to the target nucleic acid so as to form at least one primer-target hybrid, b) Subjecting each primer-target hybrid to polymerase catalysed chain extension conditions in the presence of four chain-extending nucleotides and of four chain-terminating nucleotide analogues, so as to generate a nested set of primer extension products, c) Subjecting each nested set of primer extension products to minimal fragmentation mass spectroscopy so as to generate said observed mass spectrum, wherein the following values are known with certainty: $CM^{-dA-}$, $CM^{-dC-}$, $CM^{-dG-}$, $CM^{-dT-}$, $CM^{-ddA-}$, $CM^{-ddC-}$, $CM^{-ddG-}$, $CM^{-ddT-}$, and CM0 (the mass of the primer used), wherein the calculated value CM0 is used in order to calibrate inter-peak mass difference values (OIPMD) of the observed mass spectrum, base calling cycles are carried out using the calibrated OIPMD values such that:

each called base allows mass calculation for the peak in the observed mass spectrum corresponding to said called base, and this calculated mass is then used as a further calibration point for subsequent rounds of base calling.

2. The method as claimed in claim 1, wherein the following values are known with certainty:
   $CM^{-dA-}$, $CM^{-dC-}$, $CM^{-dG-}$, $CM^{-dT-}$, $CM^{-ddA-}$, $CM^{-ddC-}$, $CM^{-ddG-}$, $CM^{-ddT-}$, CM0 (the mass of the primer used), and CM1 (the mass of the first peak beyond the primer used), and the calculated values CM0 and CM1 are used in order to calibrate OIPMD values of the observed mass spectrum.

3. The method as claimed in claim 1 wherein the following values are known with certainty:
   $CM^{-dA-}$, $CM^{-dC-}$, $CM^{-dG-}$, $CM^{-dT-}$, $CM^{-ddA}$, $CM^{-ddC-}$, $CM^{-ddG-}$, $CM^{-ddT-}$, CM0 (the mass of the primer used), and the masses (CM1-r) of the first through rth peak beyond the primer used where r is the number of residues of extension product from the primer, and the calculated value CM0, and CM1 through CMr are used in order to calibrate OIPMD values of the observed mass spectrum.

4. The method as claimed in claim 1 wherein the following values are known with certainty:
   $CM^{-dA-}$, $CM^{-dC-}$, $CM^{-dG-}$, $CM^{-dT-}$, $CM^{-ddA-}$, $CM^{-ddC-}$, $CM^{-ddG-}$, $CM^{-ddT-}$ and CM0 (the mass of the primer used), and the mass of one or more calibration compounds (of known mass), and the calculated values CM0 and the calibration compound masses) are used in order to calibrate the OIPMD values of the observed mass spectrum.

5. The method as claimed in claim 1 wherein all of the bases called are used for the calibration step.

6. The method as claimed in claim 1 wherein a rolling subset of all of the bases called are used for the calibration step.

7. The method as claimed in claim 1 wherein linear regression is used for the calibration step.

8. The method as claimed in claim 1 wherein nonlinear regression is used for the calibration step.

9. The method as claimed in claim 1 comprising the step of determining the confidence of base calling by measuring the closeness between the values for $CM^{-dA-}$, $CM^{-dC-}$, $CM^{-dG-}$, $CM^{-dT-}$ and the calibrated OIPMD values.

10. The method as claimed in claim 1 wherein a plurality of oligonucleotide primers is hybridized in step a) to the target nucleic acid so as to form a plurality of primer-target hybrids.

11. The method as claimed in claim 1 wherein an oligonucleotide primer comprises one or more residues selected from the group consisting of residues modified in the base, residues modified in the sugar, residues modified in the backbone and residues which have one or more attached intercalating groups.

12. The method as claimed in claim 1 wherein each oligonucleotide primer used in step a) is attached to a solid surface.

13. The method as claimed in claim 1 wherein each nested set of primer extension products in step c) is embedded in a matrix, from which it is desorbed and ionised by minimal fragmentation means of a laser pulse for analysis by mass spectroscopy.

14. The method as claimed in claim 13 wherein the minimal fragmentation mass spectroscopy is time-of-flight mass spectroscopy or fourier transform mass spectroscopy.

15. The method as claimed in claim 1 wherein the primer extension products, generated in step b) and subjected to minimal fragmentation mass spectrometry in step c) have been chemically charged in a predetermined manner.

16. A reaction mixture containing all four base specific chain extension nucleotides which are not labelled so as to be distinguishable from one another, and four chain termination nucleotide analogues which are not labelled so as to be distinguishable from one another.

17. The reaction mixture of claim 16, wherein the base specific chain extension nucleotides are deoxynucleoside triphosphates and the chain terminating agents are dideoxynucleoside triphosphates.

* * * * *

UNITED STATES PATENT AND TRADEMARK OFFICE
CERTIFICATE OF CORRECTION

PATENT NO. : 5,849,542
DATED : December 15, 1998
INVENTOR(S) : Michael Alan Reeve, Roland Paul Howe, and Terek Schwarz It is certified that error appears in the above-identified patent and that said Letters Patent is hereby corrected as shown below:

On the title page, under item [56],

U.S. Patent Documents: Please insert - - 5,174,962, 12/92, Brennan, 422/78 --.

Col. 4, line 13: Delete "[41]", and insert - -[4]- -.

Col. 4, line 15: Delete "Spectroscoty", and insert - -Spectroscopy- -.

Col. 4, line 55: Delete "cloud", and insert - -'cloud'- -.

Col. 10, line 20: Delete "Vested" and insert - -Vestec- -.

Col. 17, line 2: Delete "masses" and insert - -mass(es)- -.

Signed and Sealed this

Seventeenth Day of October, 2000

Attest:

Q. TODD DICKINSON

*Attesting Officer*  *Director of Patents and Trademarks*